US012592142B2

(12) United States Patent
Ten Kate et al.

(10) Patent No.: US 12,592,142 B2
(45) Date of Patent: Mar. 31, 2026

(54) MONITORING SUBJECTS AFTER DISCHARGE

(71) Applicant: KONINKLIJKE PHILIPS N.V., Eindhoven (NL)

(72) Inventors: Warner Rudolph Theophile Ten Kate, Waalre (NL); Salvatore Saporito, Rotterdam (NL); Andreas Ejupi, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 108 days.

(21) Appl. No.: 18/290,836

(22) PCT Filed: Jul. 19, 2022

(86) PCT No.: PCT/EP2022/070193
§ 371 (c)(1),
(2) Date: Jan. 22, 2024

(87) PCT Pub. No.: WO2023/001820
PCT Pub. Date: Jan. 26, 2023

(65) Prior Publication Data
US 2024/0346907 A1 Oct. 17, 2024

(30) Foreign Application Priority Data
Jul. 21, 2021 (EP) .................................... 21186966

(51) Int. Cl.
*G08B 21/18* (2006.01)
*A61B 5/00* (2006.01)
*G16H 40/67* (2018.01)

(52) U.S. Cl.
CPC .......... *G08B 21/182* (2013.01); *A61B 5/0002* (2013.01); *G16H 40/67* (2018.01)

(58) Field of Classification Search
CPC ..... G08B 21/182; G16H 40/67; A61B 5/0002
USPC ....................................................... 340/573.1
See application file for complete search history.

(56) References Cited

U.S. PATENT DOCUMENTS

| | | | | |
|---|---|---|---|---|
| 7,454,360 B2* | 11/2008 | Rosenfeld | .............. | G16H 20/10 |
| | | | | 600/300 |
| 7,986,994 B2* | 7/2011 | Stadler | ................ | G06F 12/0862 |
| | | | | 600/484 |
| 9,852,265 B1* | 12/2017 | Treacy | ................... | G16H 10/60 |
| 2006/0271409 A1* | 11/2006 | Rosenfeld | .............. | G08B 21/04 |
| | | | | 600/300 |
| 2007/0118054 A1* | 5/2007 | Pinhas | ................... | G16H 40/67 |
| | | | | 600/587 |
| 2009/0088606 A1* | 4/2009 | Cuddihy | ................ | G16H 40/67 |
| | | | | 600/300 |

(Continued)

FOREIGN PATENT DOCUMENTS

WO 2013150523 A1 10/2013

OTHER PUBLICATIONS

International Search report and Written Opinion of PCT/EP2022/070193, dated Nov. 9, 2022.

*Primary Examiner* — Zhen Y Wu

(57) ABSTRACT
A mechanism for setting one or more thresholds for post-discharge monitoring of a target subject. The thresholds are set to be time-dependent, so that the current value of the threshold depends upon a time since the target subject has been discharged from a clinical environment.

20 Claims, 4 Drawing Sheets

(56)  References Cited

U.S. PATENT DOCUMENTS

| | | | |
|---|---|---|---|
| 2010/0056875 A1* | 3/2010 | Schoenberg ......... | A61B 5/1113<br>600/300 |
| 2011/0009760 A1* | 1/2011 | Zhang ................... | G16H 10/60<br>600/529 |
| 2012/0130198 A1* | 5/2012 | Beaule .................. | G16H 50/30<br>600/300 |
| 2012/0253207 A1* | 10/2012 | Sarkar ................. | A61B 5/0004<br>600/483 |
| 2014/0187890 A1* | 7/2014 | Mensinger ............ | A61B 5/743<br>600/365 |
| 2014/0207492 A1* | 7/2014 | Farooq .................. | G16H 10/60<br>705/3 |
| 2014/0266714 A1* | 9/2014 | Becker Antley ..... | G06Q 10/107<br>340/540 |
| 2015/0042474 A1* | 2/2015 | Becker Antley ....... | G06Q 10/10<br>340/540 |
| 2016/0029971 A1* | 2/2016 | Sachdev ............. | A61B 5/7271<br>600/529 |
| 2016/0203290 A1* | 7/2016 | An ......................... | G16H 40/67<br>705/2 |
| 2017/0124279 A1* | 5/2017 | Rothman .............. | G16H 50/30 |
| 2019/0320987 A1* | 10/2019 | Halperin .............. | G16H 40/63 |
| 2020/0135334 A1 | 4/2020 | Rajasekhar et al. | |
| 2022/0023536 A1* | 1/2022 | Graham ................ | G16H 20/17 |

* cited by examiner

MONITORING SUBJECTS AFTER DISCHARGE

CROSS-REFERENCE TO PRIOR APPLICATIONS

This application is the U.S. National Phase application under 35 U.S.C. § 371 of International Application No. PCT/EP2022/070193, filed on Jul. 19, 2022, which claims the benefit of European Patent Application No. 21186966.4, filed on Jul. 21, 2021. These applications are hereby incorporated by reference herein.

FIELD OF THE INVENTION

The present invention relates to the field of monitoring subjects or patients, and in particular, to monitoring of a subject following discharge.

BACKGROUND OF THE INVENTION

When a subject is medically/clinically stable at the end of clinical care of a subject or patient, then they will be discharged. Thus, for any given clinical treatment or stay of a subject, there is a pre-discharge phase and a post-discharge phase.

However, after discharge, there is still a risk that the condition of the subject will deteriorate or will not improve/recover at an expected rate, which could lead to the subject re-entering clinical care. It has been suggested that (physiological) characteristics of a subject may be monitored following discharge from the clinical environment (i.e. during a post-discharge phase). Monitoring may be performed, for example, using remote sensors (such as electrocardiogram (ECG) measuring devices, blood pressure measuring devices, oxygenation level measuring devices, activity measuring devices, therapeutic devices, etc.), which are typically wearable devices, and/or questionnaire or self-reporting mechanisms. Monitoring the subject in this way means that a sudden change in the subject's condition can be identified and brought to a clinician's attention, e.g. to allow the clinician to intervene before significant deterioration of the subject.

One mechanism for identifying sudden changes is to set alert thresholds in condition-responsive measures that are monitored during the post-discharge phase. If an alert threshold of condition-responsive measure is breached (e.g. if an average heartrate falls below some predetermined alert threshold), then an alert or alarm can be generated for a clinician. Examples of suitable condition-responsive measures include a (change in): heartrate, respiratory rate, number of fall events, temperature, blood pressure, activity level, weight, cough rate, posture, walking speed, cognitive status and so on.

SUMMARY OF THE INVENTION

The invention is defined by the claims.

According to examples in accordance with an aspect of the invention, there is provided a computer-implemented method of setting one or more alert thresholds for alerts during a post-discharge phase of a target subject.

The computer-implemented method comprises: setting one or more alert thresholds for one or more condition-responsive measures of the target subject monitored during a post-discharge phase, wherein breaching an alert threshold generates an alert for one or more clinicians responsible for the target subject, wherein each alert threshold is configured to change responsive to a time since discharge of the target subject.

In preferred embodiments, the computer implemented method further comprises communicating or passing the one or more alert thresholds (according to the setting) to a subject monitoring system, which may be formed of one or more monitoring devices for monitoring one or more condition-responsive measures of the target subject. In particular, the monitored condition-responsive measures include the condition-responsive measures for which one or more alert threshold have been set. The subject monitoring system is a system for monitoring the subject post-discharge. That is, the monitoring system is for monitoring said one or more condition responsive measures of the subject during the post-discharge phase. In some examples, the setting of the one or more alert thresholds comprises determining settings for each of the one or more alert thresholds, and then passing or communicating these settings to the already mentioned subject monitoring system.

As the alert threshold is time-dependent, the method may include a step of determining or obtaining a time of discharge of the target subject, and communicating this to the aforementioned subject monitoring system. This may be for use in calculating a time since discharge, for use in calculating a current value of each threshold.

The present disclosure proposes a novel approach to setting alert thresholds for detecting deterioration of a subject following discharge from the hospital. Each alert threshold (which, if breached, triggers the generation of an alert) is set to be time-dependent. This approach recognizes that (following discharge) the patient's condition is expected to further improve over time. By having time-dependent alert thresholds, an expected improvement in the patient's/subject's condition can effectively be monitored.

The proposed approach thereby provides more relevant and adaptive alert thresholds for monitoring a subject after they have been discharged. Use of the proposed alert thresholds facilitates early release or discharging of the subject, as the time-dependent alert thresholds may track an expected recovery timeline of the target subject, where deviation from this timeline may be identified. Thus, in some embodiments, a value or level of each alert threshold may be configured to decrease as a function of time. In other words, the allowable range of values defined by each threshold for the one or more condition-responsive measures of the target subject is configured to decrease in size as a function of increasing time since discharge. This reflects expected improvement in patient condition, whereby the values for the monitored measures should become more stable as time elapses since discharge.

In particular, use of the adaptive or time-dependent threshold facilitates increased confidence that the subject is recovering well, i.e. according to a desired improved schedule, so that early discharge of the subject is facilitated.

An alert threshold is a value for a particular characteristic which, if breached (e.g. exceeded or fallen below), generates an alert. The alert may, for instance, be provided to one or more portable devices carried by a clinician or set of clinicians responsible for the subject or to a device in the clinical area in which the target subject was treated before discharge.

A post-discharge phase is the phase following discharge of the target subject from clinical care, e.g. discharge from a hospital, clinic and/or care home. A subject is usually only discharged when they are sufficiently medically or clinically stable to continue recovery in a home environment without substantive clinical input or intervention (i.e. is low risk). Thus, in other words, the post-discharge phase is a subject monitoring phase which takes place post-discharge, i.e. following discharge of the target subject from clinical care.

Each alert threshold may be configured to change according to a respective sequence, each entry in the respective sequence being associated with a different time since discharge of the target subject.

Thus, a time-dependent alert threshold may effectively be a sequence of alert thresholds, where progress through the sequence (i.e. a currently active alert threshold) is dependent upon a time since discharge. Each entry in the sequence of alert thresholds may be associated with a respective length of time, representing the length of time that said alert threshold is the currently active alert threshold. Similarly, each entry in the sequence of alert thresholds may be associated with a start and/or end time, representing a time at which the alert threshold starts and/or ends.

The step of setting one or more alert thresholds may comprise receiving a user input, at a user interface, setting or defining the one or more alert thresholds. In this way, the alert threshold(s) may be manually set by a clinician. This ensures that appropriate medical knowledge and experience is used in the setting of the alert thresholds.

The method may further comprise during a first predischarge phase of the target subject: monitoring values of one or more condition-responsive measures of the target subject; and displaying a visual representation of the monitored values of condition-responsive measures of the target subject at an output display. This aids a user in setting of any thresholds.

The method may comprise, during a second pre-discharge phase of the target subject: monitoring values of one or more condition-responsive measures of the target subject using one or more monitoring devices: generating one or more recommended alert thresholds for the one or more alert thresholds based on the monitored values of the condition-responsive measures.

The step of generating one or more recommended alert thresholds may comprise, for each recommended alert threshold: identifying statistical information about the associated condition-responsive measure monitored during the second pre-discharge phase; and setting the recommended alert threshold responsive to the statistical information.

The second pre-discharge phase may end at a time at which the target subject is discharged.

The second pre-discharge phase may start at a time at which a physician indicates that the target subject is in a condition for or at a predetermined time period before the time at which the target subject is discharged.

There is also proposed a computer-implemented method of monitoring a target subject during a post-discharge phase. The computer-implemented method comprises: performing any previously described method to define one or more alert thresholds, each alert threshold being associated with a respective condition-responsive measure of the target subject; monitoring, during the post-discharge phase, values of each condition-responsive measure of the target subject that is associated with an alert threshold using one or more monitoring devices; comparing, for each alert threshold, the value of the monitored condition-responsive measure associated with that alert threshold with the alert threshold; and in response to any monitored value of the monitored condition-responsive measure breaching an alert threshold associated with the monitored condition-responsive measure, generating an alert for one or more clinicians responsible for the target subject.

As the alert threshold is time-dependent, the step of comparing the value of the monitored condition-responsive measure associated with that alert threshold with the alert threshold may comprise determining or obtaining a time since discharge of the target subject, determining the current value of the alert threshold based on the determined/obtained time and comparing the current value of the monitored condition-responsive measure to the current value of the alert threshold.

There is also proposed a computer-implemented method of predicting the occurrence of alerts during a post-discharge phase of a target subject. The computer-implemented method comprises: performing a herein described method to define one or more alert thresholds, each alert threshold being associated with a respective condition-responsive measure of the target subject; obtaining historic alert data indicating the occurrence of alerts during a post-discharge phase of a set of one or more other subjects; processing the one or more alert thresholds and the historic alert data to generate predicted alert data, indicating a predicted occurrence of alerts for the target subject during the post-discharge phase; and generating one or more indicators responsive to the predicted alert data.

This embodiment provides a mechanism for predicting alert data (e.g. identifying a number or rate of alerts) that will be generated for a target subject (i.e. a particular subject) based on alert thresholds that define when alerts are generated for the target subject during a post-discharge phase. Historic alert data (for other subjects) is used to predict the number/rate of alerts that will be generated.

The proposed approach thereby allows indicators responsive to the predicted number/rate of alerts to be generated. This provides useful clinical information for assessing a number of alerts that a clinician is likely to encounter for the target subject, and thereby whether they are likely to suffer from alert fatigue and/or whether the alert thresholds are inappropriate (e.g. too sensitive, and therefore not representative of true clinical concerns). This information can be used to adjust alert thresholds for the target subject to more appropriate values in order to reduce the chance of alert fatigue and/or be more contextually and clinically relevant.

An occurrence of alerts may comprise a number of alerts, an alert rate, a number of alerts within a predetermined window of time and so on. The occurrence of alerts may further identify to which clinician each alert is provided.

The step of generating one or more indicators may comprise: obtaining clinician alert fatigue data representing a number of allowable alerts for the one or more clinicians; and processing the predicted alert data and the clinical alert fatigue data to generate a first indicator that indicates a prediction of whether the number of alerts generated for any of the one or more clinicians will exceed the number of allowable alerts for that clinician.

The computer-implemented method may further comprise generating, at a user interface, a user-perceptible alert responsive to the first indicator predicting that the number of alerts generated for any of the one or more clinicians will exceed the number of allowable alerts for that clinician.

There is also proposed a computer program product comprising computer program code means which, when executed on a computing device having a processing system, cause the processing system to perform all of the steps of any herein described method.

There is also proposed a processing system for setting one or more alert thresholds for alerts during a post-discharge phase of a target subject. The processing system is configured to set one or more alert thresholds for one or more condition-responsive measures of the target subject moni-tored during a post-discharge phase, wherein breaching an alert threshold generates an alert for one or more clinicians responsible for the target subject, wherein each alert thresh-old is configured to change responsive to a time since discharge of the target subject. The processing system may be configured to perform any herein described method, and vice versa.

In preferred embodiments, the processing system is fur-ther configured to communicate or pass the one or more alert thresholds (according to the setting) to a subject monitoring system, which may be formed of one or more monitoring devices for monitoring one or more condition-responsive measures of the target subject post discharge.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figures 1, 2:
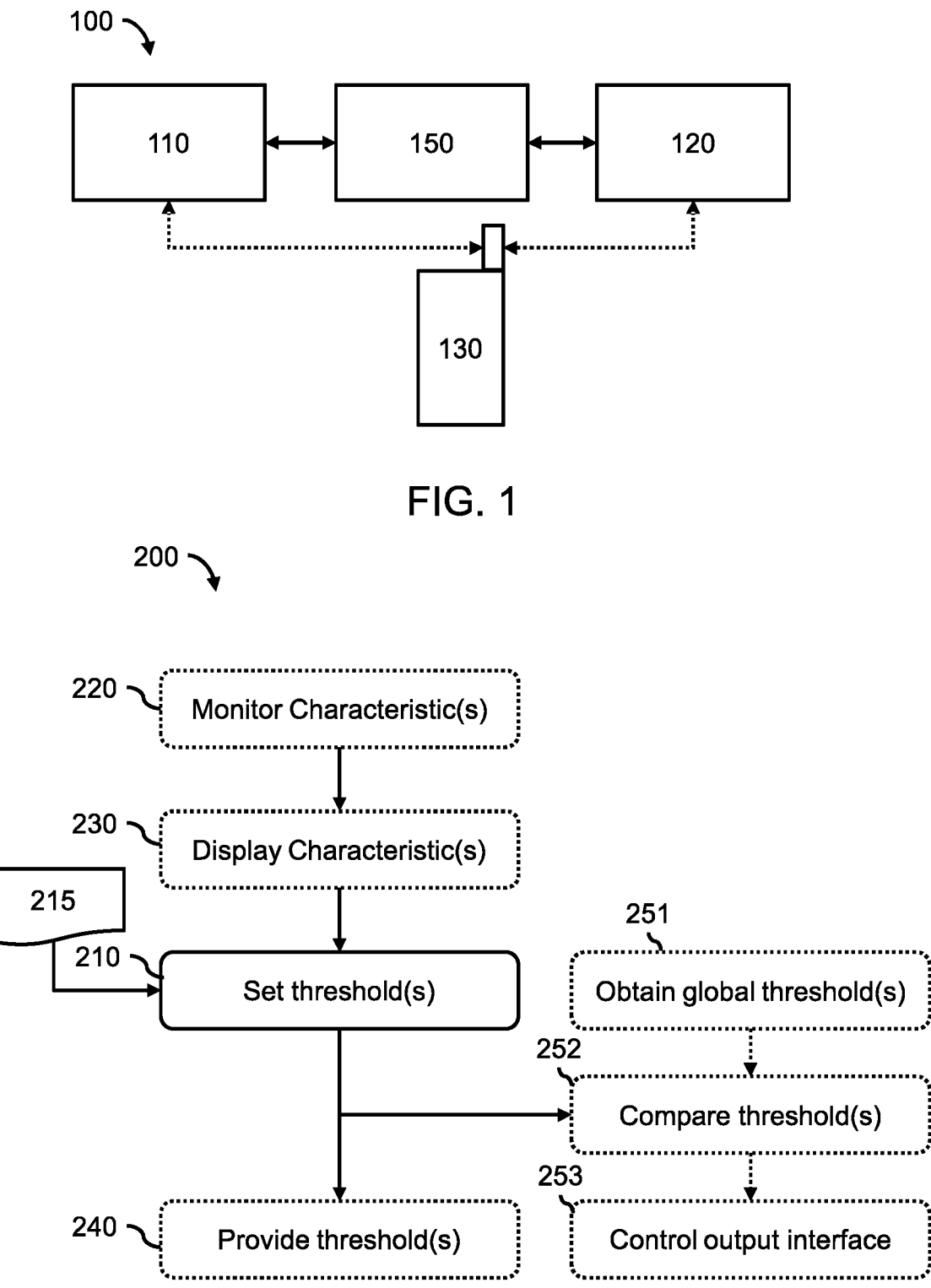
FIG. 1 provides an overview of a system in which embodiments may be employed.
FIG. 2 illustrates a method according to an embodiment.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides a mechanism for setting one or more thresholds for post-discharge monitoring of a target subject. The thresholds are set to be time-dependent, so that the current value of the threshold depends upon a time since the target subject has been discharged from a clinical envi-ronment.

Embodiments are based on a realization that a time-dependent threshold would take into account expected sub-ject improvement or changes as they recover from their stay in the clinical environment. This facilitates earlier discharg-ing of the patient, as expected trends in improvement can be taken into account (meaning that deterioration from an expected trend can be more quickly identified).

One or more embodiments may be utilized in the setting of one or more thresholds for post-discharge monitoring, and could be used in any clinical environment from where a subject is discharged, e.g. hospitals, treatment/physio-therapy centers or care homes.

In the context of the present disclosure, a condition-responsive measure is any numeric measure or indicator of a characteristic of a subject that changes responsive to a change in (health or fitness) condition of the subject. In particular, deterioration or improvement of a subject's health condition will change the condition-responsive measure.

A condition-responsive measure may comprise a (direct) measure of a particular physiological characteristic of the subject or a value derived by processing one or more values of one or more physiological characteristics (e.g. statistical information of a particular physiological characteristics, a weighted sum of different physiological characteristics etc.).

Examples of suitable condition-responsive measures include (direct) measures of physiological characteristics such as vital signs (e.g. heart rate, blood pressure, tempera-ture, respiration rate, $SpO_2$ levels and so on). Other examples of physiological characteristics include a (daily) weight, an activity pattern, a number of falls, a walking speed, a posture, sleep data (e.g. sleep stages) and so on. Some examples of physiological characteristic may relate to certain states of the subject, for instance, only during rest (e.g. resting heart rate), or during certain activities, e.g. during walking (e.g. active heart rate).

Yet other examples of condition-responsive measures include processed characteristics, e.g. statistical information on a particular (physiological) characteristics of a subject. For example, a condition-responsive measure may comprise a mean or average value of a particular physiological characteristic, e.g. obtained over a window of time having a predetermined length.

In some examples, a condition-responsive measure may be the result of a (statistical) comparison between one or more data points and one or more baseline data points, e.g. a comparison between two ECG waveforms, between two heartrate signals or between two heartrate values. For instance, a condition responsive measure may comprise cross-correlation coefficients between a waveform obtained during one period of time (e.g. in the pre-discharge phase) and a waveform obtained during another period of time (e.g. in the post-discharge phase).

Yet another condition-responsive measure may be a value indicating a likelihood that a physiological characteristic is within allowable or desirable bounds. For instance, a (log-) likelihood ratio test (LRT) may provide a value indicating a probability that a (current) value of a physiological charac-teristic belongs to a group of acceptable values (e.g. derived from healthy subjects) or non-desirable values (e.g. derived from unhealthy subjects).

A condition responsive measure may be a trend or set of data points representing change of a physiological charac-teristic over time. Thus, a condition responsive measure may be a sequence or series of data elements or values (e.g. representing a heart rate over a period of time or a respira-tory rate over a period of time and so on).

FIG. 1 provides an overview of a system 100 in which embodiments can be employed, for improved conceptual understanding.

The system 100 comprises a clinical monitoring system 110 and a non-clinical monitoring system 120, both of which monitor one or more condition-responsive measures of a subject (e.g. a patient). The clinical monitoring system monitors one or more condition-responsive measures of the subject in a clinical environment (e.g. in a hospital or care home), i.e. before the patient is discharged or in a pre-discharge phase. The non-clinical monitoring system 120 monitors one or more condition-responsive measures of the subject in a non-clinical environment (i.e. at home), i.e. after the patient is discharged from the clinical environment or in a post-discharge phase.

The non-clinical monitoring system is configured to generate an alert (or other indicator such as an alarm) in response to a particular condition-responsive measure breaching a predetermined alert threshold. For instance, an alert may be generated if a heart rate of the subject rises above a first predetermined alert threshold and/or falls below a second predetermined alert threshold. Different condition-responsive measures may be monitored and may have one or more associated predetermined alert thresholds. In particular, a threshold may be an "upper threshold" (defining the maximum allowable value before an alert is generated) or a "lower threshold (defining the minimum allowable value before an alert is generated). Any given condition-responsive measure may be tested against a lower or upper threshold or both.

Suitable examples of condition-responsive measures have been previously described. If a condition-responsive measure is one that depends upon a comparison between a data set and a baseline data set, the baseline data set may be defined in the pre-discharge phase.

Generating an alert may comprise controlling an alert signal to provide an indication that an alert threshold has been breached. The alert signal may be provided to one or more clinician interfaces that operate responsive to the alert signal.

When an alert is generated, i.e. when an alert threshold is breached, the non-clinical monitoring system may cause a clinician-perceptible output to be provided. For instance, the non-clinical monitoring system 120 may generate and provide an alert signal to a clinician interface 130 that in turn provides a perceptible alert (i.e. a visual, audio and/or haptic output) to the clinician if the alert signal indicates that an alert threshold has been breached.

The clinician interface 130 may comprise any output interface that facilitates provision of a clinician-perceptible alert to a clinician (responsible for the subject). The clinician interface may comprise a portable or handheld device (e.g. a mobile phone, pager or smart device) that responds to an alert signal provided by a non-clinical monitoring system to generate an output-such as a visual display, a vibration, a sound and so on.

The clinician interface 130 may comprise a visual, audio and/or haptic output module that generates a visual, audio and/or haptic output response to an alert signal.

The clinician-perceptible alert may prompt the clinician to take action upon the subject, e.g. to contact the subject (or their friends/family) to investigate a cause of the alert, to visit the subject and/or to recall/readmit the subject to the clinical environment.

The skilled person will also appreciate that, before discharge, the clinical monitoring system 110 may monitor one or more condition-responsive measures of the subject and generate one or more alerts (e.g. which trigger a clinician perceptible alert).

Communication between the monitoring system(s) and the clinician interface(s) may take place over any suitable communication channel, e.g. any wired or wireless channel. Suitable communication channels that may be used include channels that make use of: an infrared link, Zigbee, Bluetooth, a wireless local area network protocol such as in accordance with the IEEE 802.11 standards, a 2G, 3G or 4G telecommunication protocol, and so on. Other formats will be readily apparent to the person skilled in the art.

The present disclosure proposes a new form of alert threshold and approaches for facilitating and aiding the setting of such alert thresholds. In particular, the present disclosure proposes the concept of a time-varying alert threshold (e.g. rather than a static alert threshold) for post-discharge monitoring.

The present disclosure recognizes that (following discharge) a subject's condition is expected to gradually improve over time, i.e. will follow a certain trend of recovery. This is particularly prevalent if the subject has been discharged early.

For instance, a subject who has been treated for a stroke should further regain mobility, for example, have increased walking speed or gait stability. As a further example, a threshold for number of falls for a post-stroke subject may be non-zero in the first period after discharge. However, it is expected that as mobility improves, falls later on should disappear and if they do happen an alert should be raised (i.e. the alert threshold for number of detected falls may drop to zero over time).

The present disclosure thereby proposes approaches for setting one or more alert thresholds that change responsive to a time since discharge of the subject. Embodiments may be employed, for example, in the system 100 of FIG. 1. For instance, a processing system 150 (of the system 100) may be configured to set one or more alert threshold(s) for the monitoring system(s) by employing one or more hereafter described methods.

This approach facilitates early discharge of subjects, and in particular, subjects with a favorable recovery profile during the in-hospital phase. This is because such subjects' further recovery at home, which is expected to continue to improve over time, can be monitored accurately (e.g. following an expected improvement trend).

FIG. 2 illustrates a (computer-implemented) method 200 according to an embodiment of the invention. The method 200 may be performed by a processing system.

The method 200 comprises a step 210 of setting one or more alert thresholds for one or more condition-responsive measures of the target subject monitored during a post-discharge phase. Breaching an alert threshold generates an alert for one or more clinicians responsible for the target subject, i.e. causes a clinician-perceptible alert to be generated. As previously explained, a threshold may be an upper threshold or a lower threshold.

Step 210 is configured so that each alert threshold is configured to change responsive to a time since discharge of the target subject. In other words, step 210 may comprise setting one or more time-dependent alert thresholds for one or more condition-responsive measures that are monitored after the target subject is discharged from a clinical environment.

Step 210 may comprise setting at least one alert threshold to effectively form a sequence of alert thresholds, wherein movement through the sequence is dependent upon a time since discharge of the target subject. In this way, the alert threshold may change in discrete time steps since the target subject is discharged. The length of the discrete time steps may be predetermined and/or set by a user.

In some examples, step 210 may comprise setting at least one alert threshold to be a function (e.g. $f(t_d)$) of time $t_d$ since discharge of the target subject. Thus, the alert threshold may continuously change over time.

Step 210 may comprise receiving a user input 215 defining the one or more alert thresholds. Thus, a user may be able to define the (time-dependent) alert thresholds, e.g. based upon their experience, training and knowledge of the target subject.

In some examples, step 210 may comprise automatically defining the one or more alert thresholds. For instance, before discharge, condition-responsive measures of the target subject may be monitored in a step 220. The monitored measures may be processed to determine one or more alert thresholds for the post-discharge phase. Working examples of such embodiments are provided later in this disclosure.

The method 200 may comprise a step 220 of monitoring (values of) pre-discharge condition-responsive measures of the target subject. Step 220 may comprise obtaining and monitoring one or more sensor signals that change responsive to changes in physiological characteristics of the target subject. Example sensor signals include ECG, PPG, and accelerometer signals. Example monitored measures include vitals, such as heart rate, blood pressure, and respiration rate, as well as mobility information, such as activity level, walking speed, and posture (e.g. "time on legs"). Any other previously described measure maybe used.

As previously explained, the characteristics obtained in step 220 may be used to determine or set the (time-dependent) alert thresholds.

In some examples, the monitored pre-discharge measures may be stored, e.g. in a target subject (electronic medical record) storage system, which may form part of a clinical database.

The monitored pre-discharge measures may be used to define baseline data, e.g. for comparative purposes with later obtained post-discharge data.

The method 200 may further comprise a step 230 of providing a visual representation of the monitored (and optionally stored) measures at a user interface or output display. In some examples, step 230 may comprise providing a visual representation of the monitored values, monitored during a first pre-discharge phase, of condition-responsive measures of the target subject at an output display.

The displayed condition-responsive measures provides a clinician with an opportunity to review the condition-responsive measures and determine one or more alert thresholds for the subject. This process also allows the clinician to determine whether or not the patient is sufficiently recovered to be discharged (e.g. whether they are sufficiently stable for their recovery to continue outside of the clinical environment).

The clinician may be able to define (in the form of a user input) one or more alert thresholds for the subject in step 210. An example of this process is later described with reference to FIG. 3.

The method 200 may further comprise a step 240 of providing the one or more alert thresholds to a (non-clinical) monitoring system. The monitoring system may then be able to use the alert thresholds in determining whether to cause an alert to be generated for a clinician responsible for the subject.

The method 200 may further comprise a step 250 of obtaining global alert threshold data indicating one or more global recommended alert thresholds for the one or more condition-responsive measures. The global recommended alert thresholds are thereby derived from population data about the one or more condition-responsive measures.

The global alert thresholds may, for instance, define standard or conventionally approved thresholds for a population cohort of subjects. For instance, one or more global thresholds may represent generic unhealthy values for particular characteristics, e.g. according to literature and/or medical studies.

In some examples, one or more additional alert thresholds are set based on the global recommended alert thresholds. In particular, additional alert thresholds may be defined to be equal to the global recommended alert thresholds.

The method 200 may comprise a step 260 of comparing the global threshold(s) to the thresholds set in step 210. This may comprise, for instance, determining a difference between a global threshold for a measure and a set alert threshold for the same measure. In particular, each threshold set in step 210 may have a corresponding global alert threshold (defined in the global alert threshold data), which is defined based on population measure (i.e. not necessarily specific to the subject).

The method 200 may comprise a step 270 of controlling a user-perceptible output interface responsive to a difference between any user-identified alert threshold and a corresponding recommended alert threshold. By way of example, a user-perceptible warning may be raised when an alert threshold set in step 210 is less conservative than the corresponding global alert threshold, e.g. for an upper threshold, greater than the corresponding global threshold or for a threshold, lower than the corresponding global threshold.

This approach provides a clinician with an indicator that the set thresholds may not be appropriate for the subject. e.g. that there may be an error in the set thresholds that might cause a deterioration of the subject to be missed. Providing this information thereby reduces a likelihood that deterioration of the subject in the post-discharge phase will be overlooked.

Figure 3:
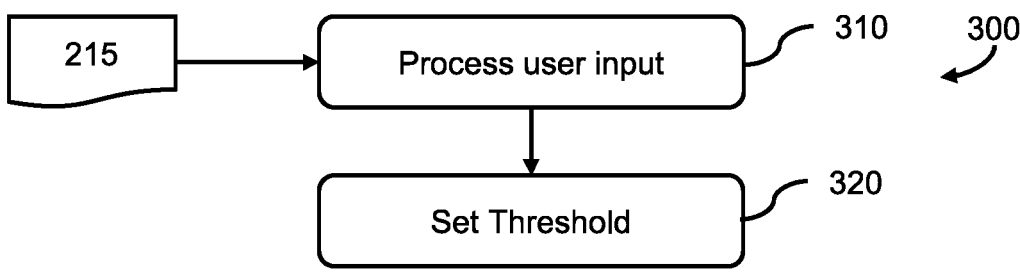
FIG. 3 illustrates a process for use in an embodiment.

FIG. 3 illustrates a process 300 of setting one or more alert thresholds according to an embodiment, which may be used to perform step 210 of the method 200. Process 300 may be performed by a processing system that sets one or more alert thresholds for a subject monitoring system.

The process 300 comprises a step 310 of receiving and processing a user input to define one or more alert thresholds. Thus, a user input 215 defines the value(s) of the alert threshold(s). This allows a clinician to make use of their experience and training in order to define the alert thresholds (e.g. responsive to displayed measures of the target subject). Each alert threshold is time-varying so that it changes responsive to a time since discharge.

Processing the user input may comprise identifying (in the user input) one or more user-defined alert thresholds. Mechanisms for communicating data via a user input are well established in the art. The user input may be carried via a user input signal, provided by a user input interface.

The process 300 then performs a step 320 of setting the one or more alert thresholds based on the alert thresholds defined by step 310. In other words, the alert threshold(s) is/are set based on a user's definition of the alert thresholds.

Process 300 may be performed after (values of) characteristics of the subject are presented to the clinician in the form of a visual representation. This allows the clinician to review the (values of) characteristics in order to make a clinical decision about the thresholds.

Figure 4:
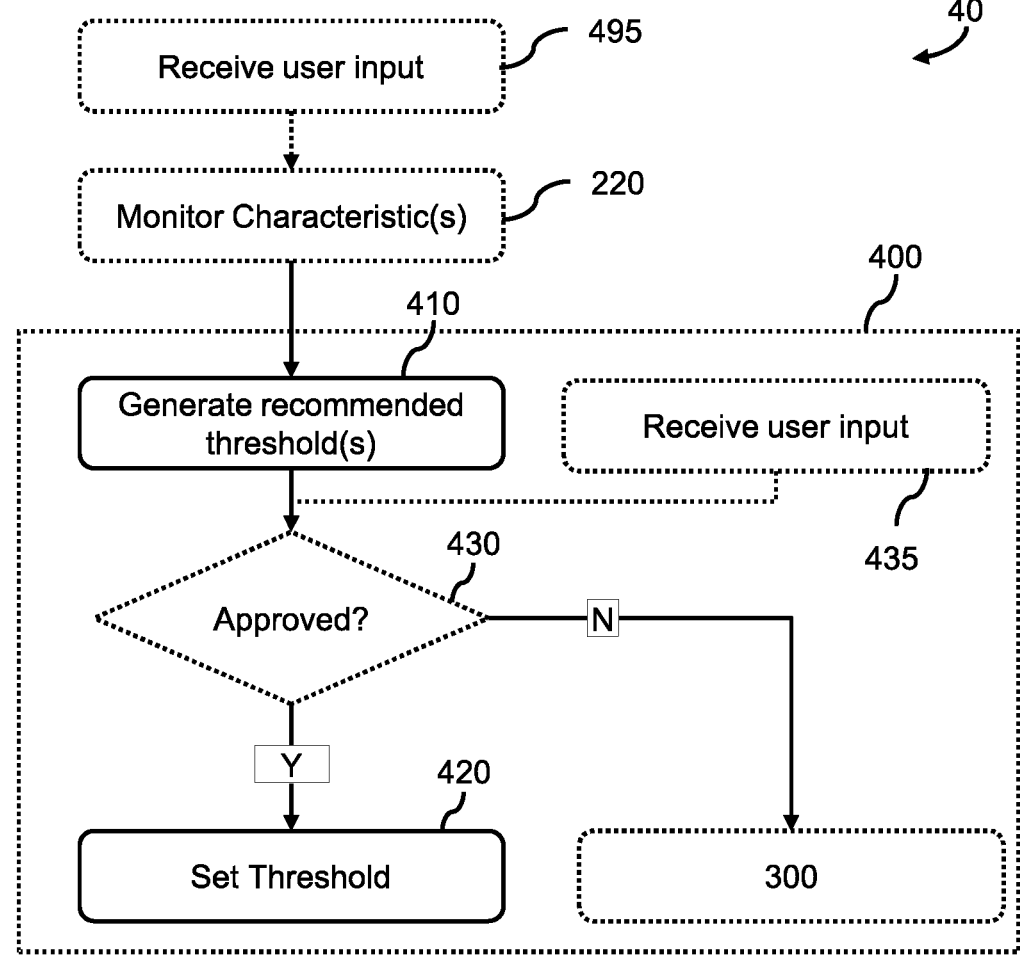
FIG. 4 illustrates a process for use in an embodiment.

FIG. 4 illustrates another process 400 of setting one or more alert thresholds according to an embodiment. Process 400 may be used to perform step 210 of method 200, previously described.

The process 400 comprises a step 410 of producing or generating one or more recommended alert thresholds.

In one example, step 410 comprises processing condition-responsive measures of the subject obtained during a (second) pre-discharge phase to produce/generate one or more recommended alert thresholds.

The second pre-discharge phase may be a phase that ends at the discharge of the target subject. The start of the second pre-discharge phase may be defined by a user input from a clinician (e.g. which triggers the start of the second pre-discharge phase), a predetermined period of time before the discharge of the target subject (e.g. the 1 day, 3 days or 5 days before the subject is discharged) or automatically (e.g. when the monitored measures of the subject meet one or more predetermined criteria).

In step 410, statistical information about the measures of the subject obtained during the (second) pre-discharge phase may be used to generate one or more recommended alert thresholds for the target subject.

By way of example, for a particular monitored measure, an alert threshold may be defined as (e.g. for a first time period immediately after discharge) being equal to a value that is twice the standard deviation away from the mean value for that measure. For a second time period (after the first time period has elapsed) the alert threshold may then be defined as being equal to 1.5 times the standard deviation away from the mean value for that measure. Thus, the recommended alert thresholds can be made time dependent based upon previously monitored measures.

Other suitable statistical information may be used to set the alert threshold(s). For instance, a median and MAD (median of absolute distances to median) of values of the condition-responsive measure during the pre-discharge phase may be used in place of the mean value and standard deviation.

Thus, more generally, step 410 may comprise determining a statistical average (Av) and a statistical variance (V) of the condition-responsive measure of the subject during the (second) pre-discharge phase. The alert threshold may be defined as being equal to $Av \pm w_t \cdot V$, where $w_t$ is a value that changes responsive to time. For instance, the value $w_t$ may be a value that decays over time since discharge, for instance:

$$w_t = w_i - \mathrm{Min}(w_{min}, t_d \cdot w_d) \tag{1}$$

where $w_i$ is an initial value for $w_t$, e.g. 2, Min(.) is a minimal value selection function, that selects the minimum value, $t_d$ is a time since discharge (e.g. in seconds, hours or days), $w_{min}$ is a value that represents a minimum allowable value for the alert threshold, and $w_d$ is a decay weight (which defines how quickly/slowly the threshold decays).

Instead of (or in addition to) varying $w_t$, the statistical average Av as well as the statistical variance V could be made to vary in the calculation of the alert threshold. For example, the average value is expected to increase steadily in the next 4 weeks, where that value represents the total duration the patient has been walking over a day.

In an alternative example, step 410 instead comprise processing condition-responsive of other (similar) subjects to the subject in order to produce one or more recommended alert thresholds. In particular, historic data of the post-discharge phase of other (similar) subjects may be processed in order to produce one or more recommended alert thresholds.

In one example, step 410 comprises obtaining historic data comprising values for condition-responsive measures of one or more similar subjects following discharge, wherein each similar subject has successfully recovered or healed. A value for a condition-responsive measure of the similar subject may be time-varying, e.g. to demonstrate how that value changes since discharge of the similar subject. A similar subject is one who shares one or more characteristics with the subject for whom the alert threshold(s) is/are being generated.

The recommended alert threshold for a particular condition-responsive measure (of the subject) may then be set based on the post-discharge values for that condition-responsive measure of the similar subject(s). For instance, the recommended alert threshold may be set to be equal to the mean of the post-discharge values of that measure for all similar subjects, ± the (weighted) variance of these values. The weight may, for instance, be equal to 2. As the post-discharge values of the similar subjects may be are time-varying, so the mean and variance of these values are time-varying, as are the recommended alert threshold(s).

Other suitable approaches for generating recommended alert thresholds by processing values of condition-responsive of the subject obtained during the pre-discharge phase and/or values of characteristics of one or more similar subjects during a post-discharge phase will be apparent to the skilled person based on the teachings provided in this disclosure, e.g. using machine-learning methods (such as neural networks) or the like.

Of course, a combination of the any herein described embodiments for step 410 could be performed, e.g. to generate different alert thresholds.

The method may then move to step 420, in which the recommended alert threshold(s) are set as the alert threshold(s) for the target subject during the post-discharge phase.

In some embodiments, step 420 is performed when step 410 is complete, i.e. is always performed.

In other examples, step 420 may only be performed in response to a user's or clinician's approval of the recommended alert threshold(s). This is illustrated by a decision step 430, which determines if a user input (received in optional step 435) indicates a clinician's approval of the recommended alert threshold(s).

Step 400 may therefore comprise a sub-step (not shown) of providing a visual representation of the recommended alert threshold(s) for review by a clinician. Step 435 may comprise receiving a user input, e.g. from a user input interface. Decision step 430 may comprise processing the user input to determine whether or not the recommended alert threshold(s) are approved by the clinician. If the recommended alert thresholds are approved, the method 400 may move to step 420. Otherwise, the method may perform an alternative process for setting the alert threshold. For instance, the method 400 may perform method 300 of defining the alert threshold(s) responsive to a user input (as previously described). Alternatively, the method 400 may repeat itself, e.g. using a different set of measures. As another alternative, the method 400 may simply discard the rejected alert threshold.

It will be appreciated that step 410 may generate a plurality of recommended alert thresholds, and that the clinician may decide to approval only a subset (i.e. not all) of the recommended alert thresholds. Thus, decision step 430 may be performed for each recommended alert threshold, with the user input received in step 435 indicating which alert threshold(s) are to be retained.

It has been previously described how step 410 may generate the recommended alert threshold(s) based on condition-responsive measures of the subject obtained during a (second) pre-discharge phase.

The condition-responsive measures may be obtained in a step 220 (previously described) in which condition-responsive measures of the target subject are monitored during the (second) pre-discharge phase. The second pre-discharge phase may be triggered responsive to a user input, e.g. received in a step 495.

The length of the second pre-discharge phase may be predetermined, e.g. of a fixed length. In other examples, the second pre-discharge phase may end responsive to a user input, e.g. when the subject is discharged.

This approach effectively allows a clinician to first set the subject's state to "trusted for discharge", at which point the condition-responsive measures are monitored (and stored). The subject can then be factually discharged (e.g. once the second pre-discharge phase has ended). There may therefore be two effective decision actions by the clinician: trusted for early discharge, and factual discharge. The second decision can be protocol based, e.g. once a predetermined period of time has elapsed, such that the clinician appears to take a single decision.

Method 400, step 220 (if performed) and step 495 (if performed) may form part of a process 40, which may effectively replace steps 220 and 210 of method 200.

Figure 5:
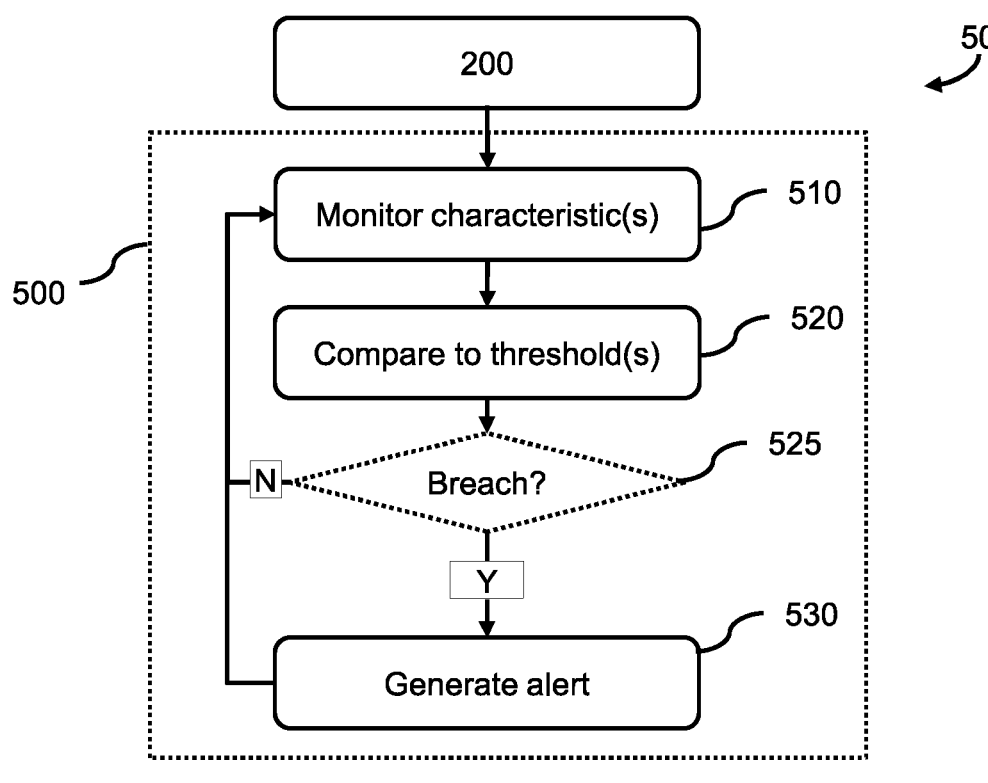
FIG. 5 illustrates a method according to an embodiment.

FIG. 5 illustrates a method 50 according to an embodiment, which includes a process 500 performed using a subject monitoring system.

The method 50 comprises performing a method 200 of generating one or more alert thresholds for alerts during a post-discharge phase of a target subject. The alert thresholds are time-dependent, as previously described, so that the value of the alert threshold changes responsive to a time since discharge of the target subject.

The generated one or more alert thresholds may then be passed to a subject monitoring system, which may be formed of one or more monitoring devices for monitoring one or more condition-responsive measures of the target subject. In particular, the monitored condition-responsive measures include the condition-responsive measures for which one or more alert threshold have been set.

The method then moves to a process 500, which takes place during a post-discharge phase of the target subject (i.e. once the subject has left the clinical environment). Process 500 may be performed by a monitoring system, e.g. by one or more monitoring devices.

Process 500 comprises a step 510 of monitoring values of each condition-responsive measure of the target subject that is associated with an alert threshold using one or more monitoring devices. Thus, the condition-responsive measure(s) of the target subject are monitored. Step 510 may be performed using at least one monitoring device, e.g. to obtain one or more values of condition-responsive measures and/or processors to process obtained physiological characteristics (obtained by the monitoring device(s) to generate the measure(s).

Various forms of condition-responsive measures have been previously described. In particular, a condition-responsive measure may comprise a measure of a physiological characteristics of the subject and/or an output produced by processing one or more physiological characteristics of the subject.

Suitable monitoring devices include wearable devices that monitor one or more physiological characteristics (e.g. $SpO_2$ sensors, heartrate sensors, blood pressure sensors and so on). Other suitable monitoring devices may include stand-alone sensors such as scales (for measuring a weight or mass of the subject).

In one working example, a condition responsive measure is generated using the following procedure.

One or more datasets are obtained, each dataset containing post-discharge monitored values of a physiological characteristic of a similar subject to the subject. The datasets are split in two categories: one for subjects healing well and the other for subjects who received additional and/or unexpected clinical intervention. For each category, (possibly after normalization (e.g. for age, severity of disease, gender, length, BMI, comorbidities, etc.)), a running distribution (or distribution curve) is determined. The distribution holds the possible values P(value|healthy) and P(value|intervention), where "P" represent the probability of the "value" belonging to the "healthy" or "intervention" group respectively. This distribution is determined at every time point of interest along the discharge phase.

A distribution may require a window of observation. The time point of interest for the distribution may be assumed to be positioned in the middle of that window.

Having established the two distributions, a likelihood ratio for a current value of the subject (under investigation) can be computed as the condition-responsive measure. This is the ratio between the probabilities of the two groups for a given value: P(value|intervention)/P(value|healthy). In some examples, the logarithm of this ratio, the so-called loglikelihood ratio (LLR), could be used as the condition-responsive measure.

The process 500 then moves to a step 520 of comparing, for each alert threshold, the value of the monitored condition-responsive measure associated with that alert threshold with the alert threshold.

As the alert threshold is time-dependent, step 520 may comprise determining or obtaining a time since discharge of the target subject, determining the current value of the alert threshold based on the determined/obtained time and comparing the current value of the monitored condition-responsive measure to the current value of the alert threshold.

Thus, an assessment may be made as to whether the monitored condition-responsive measure, and in particular the current value of the monitored measure, breaches a threshold. If the alert threshold is an upper threshold, step 520 comprises (for that threshold) determining whether the value of the monitored condition-responsive measure exceeds that alert threshold. If the alert threshold is a lower threshold, step 520 comprises (for that threshold) determining whether the value of the monitored condition-responsive measure falls below that alert threshold.

In a continuation of the working example previously described, e.g. where the condition responsive measure is an LLR value, then step 520 comprises testing the LLR value against an alert threshold. The alert threshold implies a certain choice on False Positives (intervention called while healthy) and Misses (patient considered healthy while intervention is needed). This trade-off can be decided on a patient-per-patient basis. Similarly, the trade-off may change with time since discharge. For example, if an early discharge is decided, the threshold will be chosen to have a low probability for Misses, while near completion of the discharge phase the threshold might be configured for a low False Positive probability.

The process 500 then moves to a step 530 of, in response to any monitored value of the monitored condition-responsive measure breaching an alert threshold associated with the monitored condition-responsive measure, generating an alert for one or more clinicians responsible for the target subject.

The determination of whether any alert threshold is breached may be performed in a separate decision step 525, or incorporated as part of step 520.

Step 530 of generating an alert may comprise controlling an alert signal to provide an indication that an alert threshold has been breached. The alert signal may be provided to one or more clinician interfaces that operate responsive to the alert signal.

The alert may cause a clinician-perceptible output to be provided. For instance, step 530 may comprise may generating and providing an alert signal to a clinician interface 130 that in turn provides a perceptible alert (i.e. a visual, audio and/or haptic output) to one or more clinicians responsible for the target subject if the alert signal indicates that an alert threshold has been breached. Thus, step 530 may comprise generating a perceptible alert to one or more clinicians responsible to the subject.

The present disclosure also recognizes that inappropriate alert thresholds may cause a significant number of (potentially irrelevant or non-urgent) alerts to be generated for a clinician, which can contribute to alert fatigue. There is therefore an ongoing desire to define appropriate alert thresholds for a subject to reduce the likelihood of alert fatigue.

Figure 6:
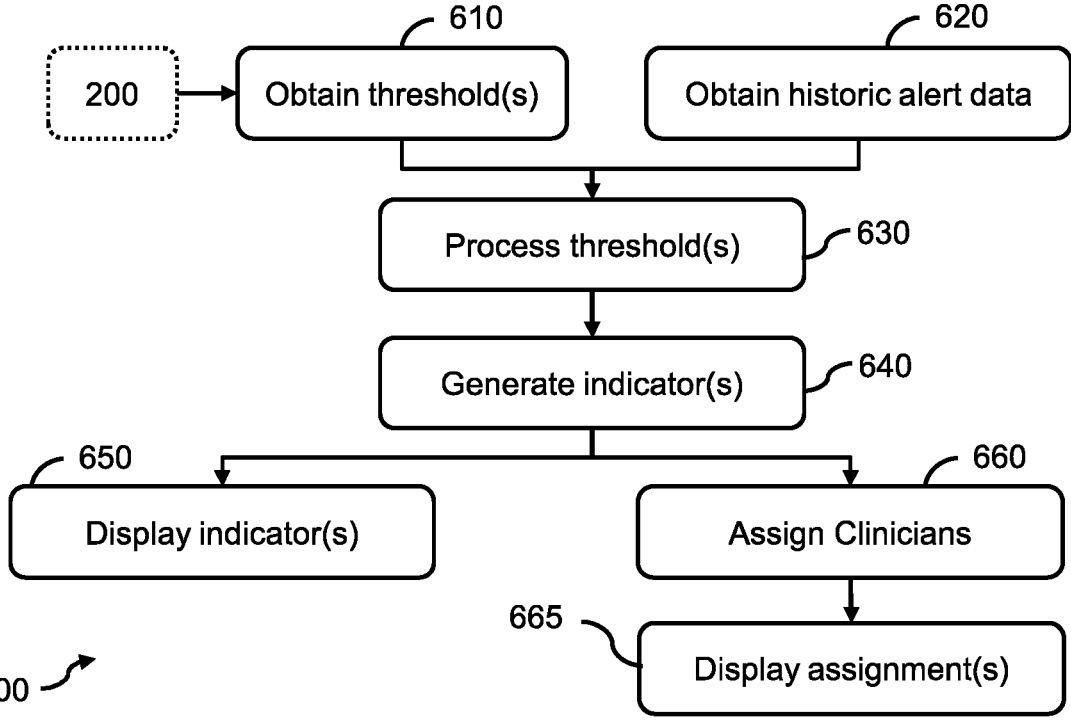
FIG. 6 illustrates a method according to an embodiment.

FIG. 6 illustrates a method 600 according to an embodiment. The method 600 predicts the occurrence of alerts during a post-discharge phase of a target subject, which can be used to mitigate or account for alert fatigue. Method 600 may be performed by a processing system, e.g. the processing system 150 illustrated in FIG. 1.

The method 600 comprises a step 610 of obtaining one or more alert thresholds, each alert threshold being associated with a respective condition-responsive measure of the target subject. The obtained alert threshold(s) may contain only the alert threshold(s) for one or more condition-responsive measures of the subject to be monitored. These alert thresholds may be generated by performing a previously described method 200. However, it is envisaged that any form of alert threshold could be used in alternative examples.

The method 600 further comprises a step 620 of obtaining historic alert data indicating the occurrence of alerts during a post-discharge phase of a set of one or more other subjects. The historic alert data may, for instance, indicate the occurrence of alerts for other subjects (e.g. including at least subjects under the responsibility of possible clinicians for the subject) for each of a plurality of different alert thresholds (and condition-responsive measures). In some circumstances, the one or more other subjects may include examples instances of the same subject currently under investigation.

The set of one or more other subjects may comprises similar subjects or subjects in a same population cohort as the target subject. In some examples, the population cohort comprises subjects that share one or more similar characteristics to the target subject, e.g. similar demographic characteristics and the like. Mechanisms for identifying similar subjects or subjects that fall within a same population cohort are well-established in the art, and may employ, for example, clustering techniques and/or algorithms.

The method also comprises a step 630 of processing the one or more alert thresholds and the historic alert data to generate predicted alert data, indicating a predicted occurrence of alerts for the target subject during the post-discharge phase. An occurrence of alerts may comprise a number of alerts, an alert rate, a number of alerts within a predetermined window of time and so on. The occurrence of alerts may further identify to which clinician each alert is provided.

Step 630 may comprise, for example, identifying (for each alert threshold for the target subject) a corresponding historic alert threshold in the historic alert data (e.g. a similar alert threshold). The occurrence of alerts for the corresponding historic alert threshold may be assigned to the alert threshold for the target subject.

The method 600 also comprises a step 640 of generating one or more indicators responsive to the predicted alert data.

Step 640 may comprise, for example, obtaining clinician alert fatigue data representing a number of allowable alerts for the one or more clinicians; and processing the predicted alert data and the clinical alert fatigue data to generate a first indicator that indicates a prediction of whether the number of alerts generated for any of the one or more clinicians will exceed the number of allowable alerts for that clinician.

In some examples, the predicted alert data and the clinician alert fatigue data are time varying, and the first indicator predicts whether, at any point or window in time during the post-discharge phase, the number of alerts generated for at least one of the one or more clinicians will exceed the number of allowable alerts for that clinician.

In at least one example, the clinical alert fatigue data contains: total allowable alert data indicating a total number of allowable alerts for the one or more clinicians; and existing alert data indicating a predicted number of alerts for other subjects under the responsibility of the one or more clinicians; and the step of processing the predicted alert data and the clinical alert fatigue data comprises: processing the predicted alert data and the existing alert data to generate predicted total alert data that indicates a predicted total number of alerts generated for the one or more clinicians; and processing the total allowable alert data and the predicted total alert data to generate the first indicator.

In this way, step 640 effectively determines (for each clinician) whether a total predicted number of alerts will exceed some predetermined threshold, thereby resulting in potential alert fatigue.

Method 600 may further comprise a step 650 of generating, at a user interface, a user-perceptible alert responsive to the first indicator predicting that the number of alerts generated for any of the one or more clinicians will exceed the number of allowable alerts for that clinician. In this way, a clinician can be alerted if it is likely that (during the post-discharge phase) more than a predetermined number of alerts will be provided to them, resulting in potential alert fatigue).

In some examples, method 600 may further comprise a step 660 of processing the predicted alert data and the clinical alert fatigue data to assign one or more clinicians to the subject during the post-discharge phase. The method may comprise a step 665 of providing a visual representation of the assigned clinicians at a user interface.

An assigned clinician is a clinician to whom a perceptible alert is provided when a monitored measure breaches a threshold. Different clinicians may be assigned for different times post-discharge so that clinician(s) to whom a perceptible alert is provided changes over time.

Step 660 may comprise assigning the clinician(s) to the subject based on the clinician alert fatigue data and may be configured so that a predicted number of alerts provided to each clinician does not exceed the number of allowable alerts for that clinician. This reduces the likelihood that any clinician will suffer from alert fatigue.

It will be appreciated that methods for generating alerts (such as those previously described) can be configured to only provide perceptible alerts to clinicians who are assigned to the subject (e.g. for a current point in time following discharge).

In some examples, step 640 generating a second indicator indicating a prediction of whether the number of alerts generated for any of the one or more clinicians will exceeds a predetermined value. A visual representation of the second indicator may be provided at a user interface, e.g. as part of step 650 and/or in place of step 650.

The skilled person would be readily capable of developing a processing system for carrying out any herein described method. Thus, each step of the flow chart may represent a different action performed by a processing system, and may be performed by a respective module of the processing system.

Embodiments may therefore make use of a processing system. The processing system can be implemented in numerous ways, with software and/or hardware, to perform the various functions required. A processor is one example of a processing system which employs one or more microprocessors that may be programmed using software (e.g., microcode) to perform the required functions. A processing system may however be implemented with or without employing a processor, and also may be implemented as a combination of dedicated hardware to perform some functions and a processor (e.g., one or more programmed microprocessors and associated circuitry) to perform other functions.

Examples of processing system components that may be employed in various embodiments of the present disclosure include, but are not limited to, conventional microprocessors, application specific integrated circuits (ASICs), and field-programmable gate arrays (FPGAs).

In various implementations, a processor or processing system may be associated with one or more storage media such as volatile and non-volatile computer memory such as RAM, PROM, EPROM, and EEPROM. The storage media may be encoded with one or more programs that, when executed on one or more processors and/or processing systems, perform the required functions. Various storage media may be fixed within a processor or processing system or may be transportable, such that the one or more programs stored thereon can be loaded into a processor or processing system.

Figure 7:
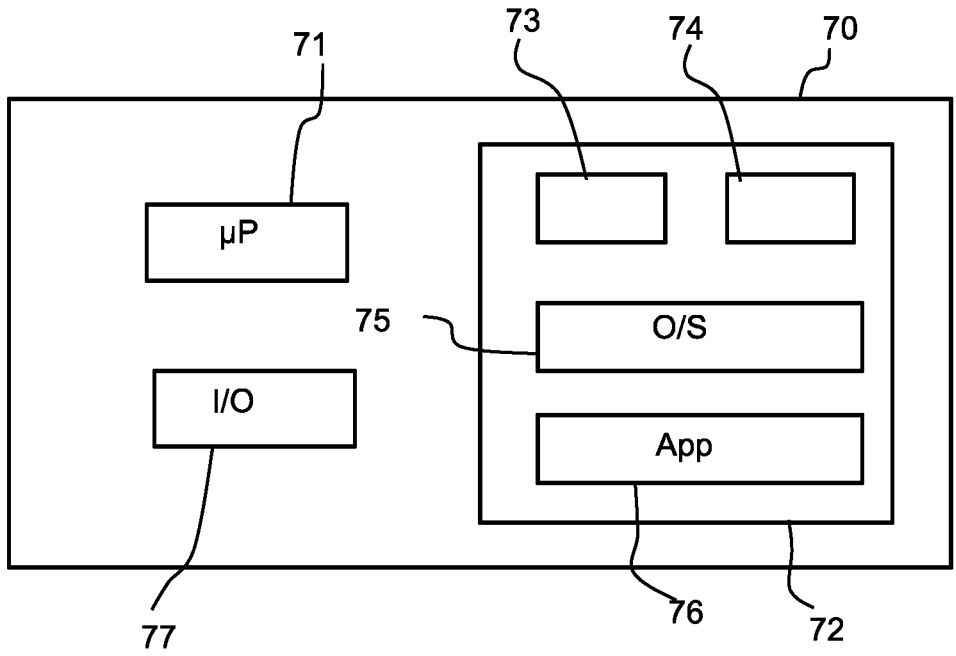
FIG. 7 illustrates a processing system.

By way of further example, FIG. 7 illustrates an example of a processing system 70 within which one or more parts of an embodiment may be employed. The processing system 70 may form the processing system 150 describes with reference to FIG. 1.

Various operations discussed above may utilize the capabilities of the processing system 70. For example, one or more parts of a system estimating a relevance of sections of unstructured textual data of a medical record may be incorporated in any element, module, application, and/or component discussed herein. In this regard, it is to be understood that system functional blocks can run on a single processing system or may be distributed over several processing systems and locations (e.g. connected via internet).

The processing system 70 includes, but is not limited to, PCs, workstations, laptops, PDAs, palm devices, servers, storages, and the like. Generally, in terms of hardware architecture, the processing system 70 may include one or more processors 71, memory 72, and one or more I/O devices 77 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 71 is a hardware device for executing software that can be stored in the memory 72. The processor 71 can be virtually any custom made or commercially available processor, a central processing unit (CPU), a digital signal processor (DSP), or an auxiliary processor among several processors associated with the processing system 70, and the processor 71 may be a semiconductor based microprocessor (in the form of a microchip) or a microprocessor.

The memory 72 can include any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 72 may incorporate electronic, magnetic, optical, and/or other types of storage media. Note that the memory 72 can have a distributed architecture, where various components are situated remote from one another, but can be accessed by the processor 71.

The software in the memory 72 may include one or more separate programs, each of which comprises an ordered listing of executable instructions for implementing logical functions. The software in the memory 72 includes a suitable operating system (O/S) 75, compiler 74, source code 73, and one or more applications 76 in accordance with exemplary embodiments. As illustrated, the application 76 comprises numerous functional components for implementing the features and operations of the exemplary embodiments. The application 76 of the processing system 70 may represent various applications, computational units, logic, functional units, processes, operations, virtual entities, and/or modules in accordance with exemplary embodiments, but the application 76 is not meant to be a limitation.

The operating system 75 controls the execution of other processing system programs, and provides scheduling, input-output control, file and data management, memory management, and communication control and related services. It is contemplated by the inventors that the application 76 for implementing exemplary embodiments may be applicable on all commercially available operating systems.

Application 76 may be a source program, executable program (object code), script, or any other entity comprising a set of instructions to be performed. When a source program, then the program is usually translated via a compiler (such as the compiler 74), assembler, interpreter, or the like, which may or may not be included within the memory 72, so as to operate properly in connection with the O/S 75. Furthermore, the application 76 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, ADA, .NET, and the like.

The I/O devices 77 may comprise at least an input interface. The input interface is configured to obtain or receive data to the processing system and may, for instance, be configured to obtain the monitored characteristics and/or user inputs. The input interface may, therefore, comprise a user input interface.

The I/O devices 77 may also comprise an output interface, which is configured to provide data for controlling an external device or passing to an external device. By way of example, the output interface may provide thresholds (and or other output data previously described) to an external device (e.g. for further processing) and/or provide display data for controlling a display to provide a visual representation of the threshold(s) and/or other output data previously described.

If the processing system 70 is a PC, workstation, intelligent device or the like, the software in the memory 72 may further include a basic input output system (BIOS) (omitted for simplicity). The BIOS is a set of essential software routines that initialize and test hardware at startup, start the O/S 75, and support the transfer of data among the hardware devices. The BIOS is stored in some type of read-only-memory, such as ROM, PROM, EPROM, EEPROM or the like, so that the BIOS can be executed when the processing system 70 is activated.

When the processing system 70 is in operation, the processor 71 is configured to execute software stored within the memory 72, to communicate data to and from the memory 72, and to generally control operations of the processing system 70 pursuant to the software. The application 76 and the O/S 75 are read, in whole or in part, by the processor 71, perhaps buffered within the processor 71, and then executed.

When the application 76 is implemented in software it should be noted that the application 76 can be stored on virtually any processing system readable medium for use by or in connection with any processing system related system or method. In the context of this document, a processing system readable medium may be an electronic, magnetic, optical, or other physical device or means that can contain or store a processing system program for use by or in connection with a processing system related system or method.

The application 76 can be embodied in any processing system-readable medium for use by or in connection with an instruction execution system, apparatus, or device, such as a processing system-based system, processor-containing system, or other system that can fetch the instructions from the instruction execution system, apparatus, or device and execute the instructions. In the context of this document, a "processing system-readable medium" can be any means that can store, communicate, propagate, or transport the program for use by or in connection with the instruction execution system, apparatus, or device. The processing system readable medium can be, for example but not limited to, an electronic, magnetic, optical, electromagnetic, infrared, or semiconductor system, apparatus, device, or propagation medium.

Figure 8:
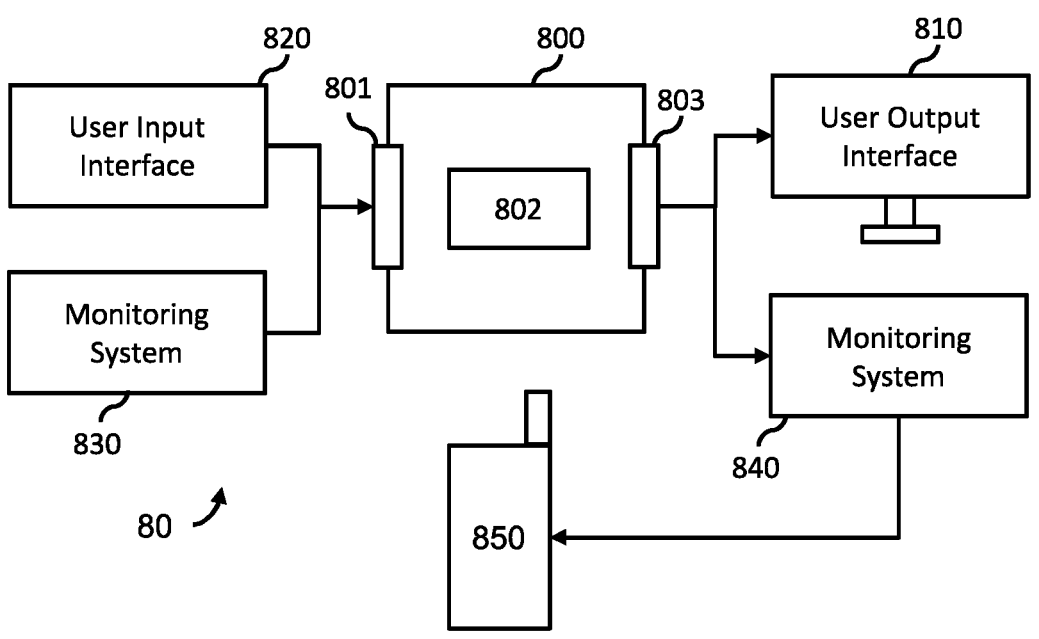
FIG. 8 illustrates a system including a processing system.

FIG. 8 illustrates a system 80 according to an embodiment.

The system 80 comprises a processing system 800, which may be embodied as the processing system 70 described with reference to FIG. 7. Other suitable examples of a processing system will be apparent to the skilled person.

The system 80 may also comprise a (first) user output interface 810 and/or a user input interface 820. The system may also comprise a first monitoring system 830 (for monitoring one or more characteristics during a pre-discharge phase) and/or a second monitoring system 840 (for monitoring one or more characteristics during a post-discharge phase).

The processing system 800 is configured to set one or more alert thresholds for one or more condition-responsive measures of the target subject monitored during a post-discharge phase, wherein breaching an alert threshold generates an alert for one or more clinicians responsible for the target subject, wherein each alert threshold is configured to change responsive to a time since discharge of the target subject.

The processing system 800 may comprise an input interface 801. The input interface may be configured to obtain monitored measures or characteristics of the subject (e.g. for processing), e.g. from the first monitoring system 830 and/or user input(s) from the user input interface 820.

The processing system 800 may comprise a processor 802 configured to set one or more alert thresholds for one or more condition-responsive measures of the target subject monitored during a post-discharge phase, wherein breaching an alert threshold generates an alert for one or more clinicians responsible for the target subject, wherein each alert threshold is configured to change responsive to a time since discharge of the target subject.

The processing system 800 and/or system 80 may be configured to perform any other method herein described.

For example, the processing system 800 may be configured to provide the threshold(s) to the user output interface and/or second monitoring system 840, e.g. via an output interface 803 of the processing system. In some examples, a visual representation of the thresholds is provided at the user output interface 820 using a control signal for controlling the operation of the user output interface.

System 80 may further comprise a clinician interface 850, which can provide a perceptible alert to one or more clinicians responsible for the target subject. The second monitoring system 840 may be configured to control the clinician interface to generate a perceptible alert responsive to a monitored measure breaching a threshold (set by the processing system 800).

The clinician interface 130 may comprise any output interface that facilitates provision of a clinician-perceptible alert to a clinician (responsible for the subject). The clinician interface may comprise, for instance, a portable or handheld device (e.g. a mobile phone, pager or smart device) that responds to an alert signal provided by a non-clinical monitoring system to generate an output-such as a visual display, a vibration, a sound and so on.

It will be understood that disclosed methods are preferably computer-implemented methods. As such, there is also proposed the concept of a computer program comprising code means for implementing any described method when said program is run on a computer, such as a computer. Thus, different portions, lines or blocks of code of a computer program according to an embodiment may be executed by a computer or computer to perform any herein described method. In some alternative implementations, the functions noted in the block diagram(s) or flow chart(s) may occur out of the order noted in the figures. For example, two blocks shown in succession may, in fact, be executed substantially concurrently, or the blocks may sometimes be executed in the reverse order, depending upon the functionality involved.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a processing system program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The invention claimed is:

1. A computer-implemented method of setting one or more alert thresholds for alerts during a post-discharge phase of a target subject, the computer-implemented method comprising:

setting the one or more alert thresholds for one or more condition-responsive measures of the target subject monitored during the post-discharge phase, wherein breaching an alert threshold generates an alert for one or more clinicians responsible for the target subject, associate each alert threshold to a time since discharge to change the alert threshold, communicating the one or more alert thresholds to a subject monitoring system formed of one or more monitoring devices for monitoring the one or more condition-responsive measures of the target subject during the post discharge phase, calculate a time since discharge of the target subject, and automatically determine whether to change an alert threshold based on the time since discharge associated with the alert threshold and the calculated time since discharge of the target subject.

2. The computer-implemented method of claim 1, wherein each alert threshold is configured to change according to a respective sequence, each entry in the respective sequence being associated with a different time since discharge of the target subject.

3. The computer-implemented method of claim 1, wherein setting the one or more alert thresholds comprises receiving a user input, at a user interface, setting the one or more alert thresholds.

4. The computer-implemented method of claim 1, further comprising, during a first pre-discharge phase of the target subject:

monitoring values of the one or more condition-responsive measures of the target subject; and displaying a visual representation of the monitored values of the one or more condition-responsive measures of the target subject at an output display.

5. The computer-implemented method of claim 1, further comprising, during a second pre-discharge phase of the target subject:

monitoring values of the one or more condition-responsive measures of the target subject using the one or more monitoring devices;

generating one or more recommended alert thresholds for the one or more alert thresholds based on the monitored values of the one or more condition-responsive measures.

6. The computer-implemented method of claim 5, wherein generating the one or more recommended alert thresholds comprises, for each recommended alert threshold:

identifying statistical information about an associated condition-responsive measure monitored during the second pre-discharge phase; and setting the recommended alert threshold responsive to the statistical information.

7. The computer-implemented method of claim 5, wherein the second pre-discharge phase ends at a time at which the target subject is discharged.

8. The computer-implemented method of claim 7, wherein the second pre-discharge phase starts at a time at which the target subject is in a condition for discharge.

9. The computer-implemented method of claim 7, wherein the second pre-discharge phase starts at a predetermined time period before the time at which the target subject is discharged.

10. The computer-implemented method of claim 1, further comprising:

monitoring, during the post-discharge phase, values of each condition-responsive measure of the target subject that is associated with an alert threshold using the one or more monitoring devices;

comparing, for each alert threshold, the value of the monitored condition-responsive measure associated with the alert threshold; and in response to a monitored value of the monitored condition-responsive measure breaching an alert threshold associated with the monitored condition-responsive measure, generating an alert for one or more clinicians responsible for the target subject.

11. The computer-implemented method of claim 1, further comprising:

obtaining historic alert data indicating an occurrence of alerts during a historic post-discharge phase of a set of one or more other subjects;

processing the one or more alert thresholds and the historic alert data to generate predicted alert data, indicating a predicted occurrence of alerts for the target subject during the post-discharge phase; and generating one or more indicators responsive to the predicted alert data.

12. The computer-implemented method of claim 11, wherein generating the one or more indicators comprises:

obtaining clinician alert fatigue data representing a number of allowable alerts for the one or more clinicians; and processing the predicted alert data and the clinical alert fatigue data to generate a first indicator that indicates a prediction of whether the number of alerts generated for a clinician of the one or more clinicians will exceed the number of allowable alerts for the clinician.

13. The computer-implemented method of claim 12, further comprising generating, at a user interface, a user-perceptible alert responsive to the first indicator predicting that the number of alerts generated for the clinician of the one or more clinicians will exceed the number of allowable alerts for that the clinician.

14. A non-transitory computer-readable storage medium having stored a computer program comprising instructions, which, when executed by a processor, cause the processor to:

set one or more alert thresholds for one or more condition-responsive measures of a target subject monitored during a post-discharge phase, wherein breaching an alert threshold generates an alert for one or more clinicians responsible for the target subject;

associate each alert threshold to a time since discharge to change the alert threshold, communicate the one or more alert thresholds to a subject monitoring system formed of one or more monitoring devices for monitoring the one or more condition-responsive measures of the target subject during the post discharge phase;

calculate a time since discharge of the target subject; and automatically determine whether to change an alert threshold based on the time since discharge associated with the alert threshold and the calculated time since discharge of the target subject.

15. A processing system for setting one or more alert thresholds for alerts during a post-discharge phase of a target subject, the processing system comprising:

a processor configured to:

set the one or more alert thresholds for one or more condition-responsive measures of the target subject monitored during the post-discharge phase, wherein breaching an alert threshold generates an alert for one or more clinicians responsible for the target subject, associate each alert threshold to a time since discharge to change the alert threshold, communicate the one or more alert thresholds to a subject monitoring system formed of one or more monitoring devices for monitoring the one or more condition-responsive measures of the target subject during the post-discharge phase;

calculate a time since discharge of the target subject, and automatically determine whether to change an alert threshold based on the time since discharge associated with the alert threshold and the calculated time since discharge of the target subject.

16. The processing system of claim 15, wherein each alert threshold is configured to change according to a respective sequence, each entry in the respective sequence being associated with a different time since discharge of the target subject.

17. The processing system of claim 15, further comprising:

a user interface configured to receive a user input to set the one or more alert thresholds.

18. The processing system of claim 15, wherein the processor is further configured to, during a first pre-discharge phase of the target subject:

monitor values of the one or more condition-responsive measures of the target subject; and display a visual representation of the monitored values of the one or more condition-responsive measures of the target subject at an output display.

19. The processing system of claim 15, wherein the processor is further configured to, during a second pre-discharge phase of the target subject:

monitor values of the one or more condition-responsive measures of the target subject using the one or more monitoring devices;

generate one or more recommended alert thresholds for the one or more alert thresholds based on the monitored values of the one or more condition-responsive measures.

20. The processing system of claim 19, wherein, to generate the one or more recommended alert thresholds, the processor is further configured to, for each recommended alert threshold:

identifying statistical information about an associated condition-responsive measure monitored during the second pre-discharge phase; and setting the recommended alert threshold responsive to the statistical information.

* * * * *